(12) United States Patent
Early et al.

(10) Patent No.: US 10,974,217 B2
(45) Date of Patent: Apr. 13, 2021

(54) RADIAL-FLOW REACTOR APPARATUS

(71) Applicant: JOHNSON MATTHEY DAVY TECHNOLOGIES LIMITED, London (GB)

(72) Inventors: Simon Robert Early, London (GB); Simon Graham, London (GB); Paul Wise, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 16/628,335

(22) PCT Filed: Jun. 13, 2018

(86) PCT No.: PCT/GB2018/051601
§ 371 (c)(1),
(2) Date: Jan. 3, 2020

(87) PCT Pub. No.: WO2019/008316
PCT Pub. Date: Jan. 10, 2019

(65) Prior Publication Data
US 2020/0147572 A1    May 14, 2020

(30) Foreign Application Priority Data
Jul. 7, 2017 (GB) ...................................... 1710924

(51) Int. Cl.
*B01J 8/02* (2006.01)
*B01J 8/06* (2006.01)
*C07C 29/152* (2006.01)

(52) U.S. Cl.
CPC ............. *B01J 8/0214* (2013.01); *B01J 8/065* (2013.01); *C07C 29/152* (2013.01); *B01J 2208/00884* (2013.01); *B01J 2208/00938* (2013.01)

(58) Field of Classification Search
CPC .............................. B01J 8/0214; B01J 8/065; B01J 2208/00884; B01J 2208/00938;
(Continued)

(56) References Cited

U.S. PATENT DOCUMENTS 4,276,265 A    6/1981   Gillespie
4,374,094 A    2/1983   Farnham
(Continued)

FOREIGN PATENT DOCUMENTS

EP          0062716 A1    10/1982
WO       2008073743 A1     6/2008

OTHER PUBLICATIONS

PCT/GB2018/051601, International Search Report dated Dec. 9, 2018.
PCT/GB2018/051601, Written Opinion dated Dec. 9, 2018.

*Primary Examiner* — Huy Tram Nguyen
(74) *Attorney, Agent, or Firm* — BakerHostetler

(57) ABSTRACT

A device suitable for use as a distributor or collector in a radial-flow reaction vessel is described, comprising an open end and a plurality of rigid columnar portions, each columnar portion comprising a cylindrical outer screen formed from parallel spaced wires and a perforate inner screen fixed to the outer screen, said inner screen formed from a plurality of adjacent perforate support members that support the spaced wires, wherein the rigid columnar portions further comprise means for controlling a flow of a gaseous process fluid to or from the device. The device may be used in radial-flow vessels used in chemical processes such as methanol synthesis.

18 Claims, 3 Drawing Sheets

(58) Field of Classification Search
CPC ... B01J 2219/00162; B01J 2219/00164; C07C 29/152
USPC ........................................................ 422/220
See application file for complete search history.

(56) References Cited

U.S. PATENT DOCUMENTS

| | | |
|---|---|---|
| 4,374,095 A | 2/1983 | Legg et al. |
| 4,421,723 A | 12/1983 | Farnham |
| 4,452,761 A | 6/1984 | Farnham |
| 2008/0107575 A1 | 5/2008 | Vetter et al. |
| 2008/0145288 A1 | 6/2008 | Koves |
| 2009/0211965 A1 | 8/2009 | Parr et al. |
| 2010/0288676 A1 | 11/2010 | Senetar |
| 2014/0128654 A1 | 5/2014 | Fang et al. |
| 2016/0121289 A1 | 5/2016 | Combes |
| 2016/0136602 A1 | 5/2016 | Bazer-Bachi et al. |
| 2016/0355399 A1 | 12/2016 | Pach et al. |

RADIAL-FLOW REACTOR APPARATUS

CROSS-REFERENCE TO RELATED APPLICATIONS

This application is the National Stage of International Patent Application No. PCT/GB2018/051601 filed Jun. 13, 2018, which claims priority to Great Britain Patent Application No. 1710924.0, filed Jul. 7, 2017, the entire disclosures of both of which are incorporated herein by reference for any and all purposes.

This invention relates to distribution or collection apparatus suitable for use in a radial flow vessel, a radial flow vessel including the apparatus and a process using the apparatus in a radial-flow vessel.

Radial flow vessels are well known and generally comprise a domed cylindrical shell with a process fluid inlet and a process fluid outlet. A central perforate distributor or collector, which is typically cylindrical, is connected to the inlet or outlet and extends along the longitudinal axis of the vessel from one end towards the other to provide a central void to which or from which a process fluid may flow. A peripheral void, which may be continuous or discontinuous, is also provided from which or to which a process fluid may flow to the outlet or inlet. A bed of catalyst is typically provided between the central and peripheral voids. A process fluid entering the vessel through the inlet may pass to the peripheral void, then radially inwards through the bed of catalyst to the central void, in which case the central cylinder may be termed a collector, and then from the central void to the outlet. Alternatively, the process fluid entering the vessel through the inlet may pass to the central void, in which case the central cylinder may be termed a distributor, then radially outwards through the bed of catalyst to the peripheral void, and then from the peripheral void to the outlet. Such vessels are described, for example, in U.S. Pat. No. 4,374,094.

The central distributor or collector in these vessels needs to be strong to deal with the weight of catalyst bed and able to cope with expansion and contraction of the bed during use. The design is often a simple one in which a cylinder is formed by rolling and welding sheet metal in which typically many thousands of holes have been drilled. However, fabrication of such designs is slow and the weld produces a portion in which there are no perforations resulting in uneven flow of process fluid. This results in parts of the catalyst or sorbent bed with uneven flow. Furthermore, conventional designs typically have a small perforation size, e.g. 2 mm, which can become blocked thereby reducing the effectiveness of the device.

Variations of the simple perforate cylinder design are known. For example, U.S. Pat. No. 4,421,723 and U.S. Pat. No. 4,452,761 disclose a fixed bed radial flow reactor with a perforated central pipe, which is in turn surrounded by a screen. U.S. Pat. No. 4,374,094 discloses a design where a tapered screen is provided about the central cylindrical collector or the collector itself is tapered. In this latter arrangement, the collector comprises a single screen of spaced wedge-shaped vertical bar members welded onto hoop members. These arrangements suffer from the same disadvantages arising from the use of a perforate cylinder design.

Furthermore, inside a distributor there is an increase in pressure as the process fluid decelerates from the highest axial velocity at the open end or ends to a zero axial velocity, either at the closed end, or at an intermediate point for a design with two open ends. There is an analogous decrease in pressure inside a collector as the fluid slowly accelerates from zero axial velocity to a maximum axial velocity at the open end or ends. These effects are described by the Bernoulli Equation, well-known in the field of fluid dynamics. Where the process fluid is a gas, the static head term is small and for both distributor and collector the lowest pressure is located near the open end or ends, where the velocity is greatest. These pressure variations cause differences in the process fluid velocity and so flow along the length of the distributor or collector, which is undesirable.

The Applicant has found an arrangement of screens that offers a greater flexibility in design than the prior art designs and overcomes the problem of variations in process fluid velocity.

We have made a device that overcomes the problems with the previous designs.

Accordingly, the invention provides a device suitable for use as a distributor or collector in a radial-flow reaction vessel, comprising an open end and a plurality of rigid columnar portions, each columnar portion comprising a cylindrical outer screen formed from parallel spaced wires and a perforate inner screen fixed to the outer screen, said inner screen formed from a plurality of adjacent perforate support members that support the spaced wires, wherein the rigid columnar portions further comprise means for controlling a flow of a gaseous process fluid to or from the device.

The invention further provides a radial-flow vessel containing the device and a process using the device in a radial-flow vessel.

Whereas the device may be used in radial-flow vessels containing a fixed bed of particulate catalyst, it may also be used in radial-flow vessels containing a fixed bed of particulate sorbent. By the term "sorbent" we include adsorbent and absorbent.

The device comprises a plurality of rigid columnar portions. The diameter of the portions is desirably the same. Preferably the diameter is in the range 0.45-0.65 metres as this allows an operator to fit within the device during catalyst loading. The length of the portions may be in the range 1-3 metres, preferably 1.5-2.0 metres. The portions may have the same length or have different lengths. In a preferred arrangement, the lengths of adjacent portions decrease from one end of the device to the other. This has the advantage that risk of installing the portions in the wrong order is reduced.

In use, the process fluid may be fed to one end of the device, in which case the device comprises an open end and a closed end opposite the open end. Alternatively, the process fluid may be fed to both ends of the device in which case the device comprises two open ends opposite each other. The device is particularly suited to operation in a radial flow vessel having a single inlet for process fluid and so is preferably a device having an open end and a closed end opposite the open end.

The cylindrical outer screen is formed from parallel spaced wires. The outer screen has openings between the wires that are sized to allow process fluid to pass through it but prevent catalyst or sorbent particles from passing through it into the device. The maximum width of the openings in the outer screen may usefully be in the range 0.5-10 mm depending on the particle size of the catalyst or sorbent. Maximum spacings in the range 0.5-2.5 mm are particularly suitable. The outer screen is desirably fabricated from a suitably robust material such as steels, including stainless steels.

The wires may be circular and arranged perpendicular to the longitudinal axis of the cylinder. Alternatively, the wires may be linear and arranged parallel to the longitudinal axis of the cylinder. Alternatively, the wires may be spirally wound around the longitudinal axis of the cylinder.

The wires are supported on the perforate support members. The angle between the wires and support members may be 60 to 120 degrees, preferably 80-100 degrees, and is especially about 90 degrees as this produces a high-strength device. Thus, preferably the support members are arranged perpendicular to the parallel spaced wires. Where the wires are arranged perpendicular to the longitudinal axis of the cylinder, the perforate support members are preferably arranged parallel to the longitudinal axis of the cylinder. Where the wires are arranged parallel to the longitudinal axis of the cylinder, the perforate support members are preferably arranged perpendicular to the longitudinal axis of the cylinder. In this arrangement, when installed, the wires forming the outer screen on the device in this arrangement are typically vertical. This has the advantage that catalyst or sorbent in contact with the wires is less likely to be damaged in contact with the wires upon expansion and contraction of the bed. Where the wires are spirally wound around the longitudinal axis of the cylinder, the perforate support members are preferably arranged at an angle of 0-90 degrees to the longitudinal axis of the cylinder, i.e. parallel or perpendicular to the longitudinal axis, or an angle in between that suitably supports the wires.

The cross-section of the wires may be circular, square, rectangular, triangular or polygonal. Preferably the wires have a triangular or wedge-shaped cross-section. A particularly suitable outer screen is formed from V-wire. Such a material is commercially available, for example as Vee-Wire® available from Johnson Screens. The triangular or wedge-shaped bars or wires are arranged desirably with the apex of the triangle or wedge faces directed inwardly towards the centre of the device. This prevents jamming of catalyst or sorbent particles in the outer screen, which is undesirable. The maximum width of the bars or wires may be in the range 1-5 mm.

The outer screen is fixed to the inner screen, preferably by welding.

The inner screen is formed from a plurality of adjacent perforate support members that support the spaced wires. The inner screen is desirably fabricated from a suitably robust material such as steels, including stainless steels. The support members are adjacent but may be spaced apart, although this is less preferred as the strength of the device may be reduced. Furthermore, if spaced apart, the spacing is preferably such that process fluid may pass through but not catalyst or sorbent particles that may have penetrated the outer screen. In a particularly preferred arrangement, the support members are fixed to each other, which provides enhanced strength to the device. Fixing may be by welding or other suitable fixing methods.

The support members desirably are open so that they provide channels through which a process fluid may pass to or from the outer screen. The Applicant has found that using open support members to fabricate the inner screen offers a far greater flexibility in device design that the prior art designs. Compared to solid rods or bars, such support members offer improved flow of process fluid through the device and save weight. The channels may be provided by each support member having two spaced attachment points and a curved or polygonal portion connecting the attachment points and extending towards the interior of the device. The channels may be conveniently provided by a support member having a cross-section selected from a semi-circle, an L-section comprising first and second flanges or a C-section comprising first and second flanges separated by a web, each flange optionally having a lip. The flanges in an L section, may be at an angle of 45-135 degrees. The flanges in a C-section may be at right angles to the web or the angle may be between 90 and 135 degrees. The length of the web may be in the range 10-150 mm. The flanges may have lengths in the range 10-100 mm. Lips, if included, may have a length in the range 1-10 mm. The thickness of the web, flanges and lips may be in the range 1-5 mm. Designs where the support members are formed from perforate C-sections are particularly preferred. C-sections, also termed C-channels, track sections or rack sections are commercially available. The channel maximum width may be in the range 10-150 mm, preferably 10-100 mm. Thus, for a support member having a semi-circular cross-section, the diameter may be in the range 10-150 mm, preferably 10-100 mm. Similarly, for a support member having a C-section cross section with flanges at about 90 degrees to the web, the width between the flanges or lips may be in the range 10-150 mm, preferably 10-100 mm. Using such structures as the support members reduces weight compared to the prior art solid hoops but produces a high strength device equivalent to the previous designs.

The support members comprise a plurality of perforations thereby forming an inner perforate screen. The perforations are suitably present in an opposed face to the inner screen, i.e. a face of the inner screen facing the outer screen. The perforations may be circular holes or other shapes such as squares or rectangles. The perforations may be punched rather than drilled, thereby speeding up the fabrication. The perforations may have a maximum width, e.g. a diameter, in the range 2-10 mm, preferably 3-7 mm. Larger perforations in the inner screen are possible because the outer screen provides a first barrier to the catalyst or sorbent. Larger perforations are less likely to block and are easier to clean. In addition, using larger perforations requires fewer perforations to be made further speeding up the fabrication.

The device has at least one open end to allow flow of process fluid into or out of the device. The open end may have a diameter equal to or less than the diameter of the outer screen. The device may have two open ends. Alternatively, the device may comprise an open end and a closed end. A closed end may, for example, be provided by fixing a non-perforate plate to the inner and outer screens. The closed end may be fabricated as part of the device or may be formed upon installation into the radial-flow vessel by connecting the outer and inner screens to a suitable plate within the reactor. In a vertical vessel, the closed end may be at the top or the bottom of the catalyst bed. In a preferred arrangement, the open end is adjacent the top of the catalyst bed and the closed end formed near the bottom.

The device according to the present invention further comprises means for controlling the flow of a gaseous process fluid to or from the device.

In one arrangement, the means for controlling the flow of a gaseous process fluid to or from the device is to provide a greater number and/or a larger size and/or a smaller spacing of the perforations in the inner screen in a portion adjacent an open end. Thus, in a portion adjacent an open end, the perforations in the inner screen may be larger in size than the perforations in the adjacent portion. Additionally or alternatively, in a portion adjacent an open end, the number of perforations in the inner screen may be greater than the number of perforations in the adjacent portion. Additionally or alternatively, in a portion adjacent an open end, the spacing of the perforations in the inner screen may be smaller than the spacing of perforations in the adjacent portion.

The vertical pitch or spacing of the perforations may conveniently be fixed by the appropriate sizing of the support members. Thus the support members may be in the range 10-150 mm in height, with perforations running along the mid-point. Furthermore, the vertical pitch can be readily altered by omitting perforations in adjacent support members. In this way, the vertical pitch can be altered to twice or even three times the support width. The circumferential pitch of the perforations or spacing of the perforations along the support members is also readily adjusted. The circumferential pitch may be the larger than in conventional designs. The spacing of the circumferential perforations may be in the range 10-150 mm. The vertical and circumferential pitch may both be readily altered in the present device. The perforations are preferably arranged in a triangular pattern. Where used to improve fluid distribution to the catalyst or sorbent, the total perforation area may be in the range 0.5-5% of the surface area of the inner screen, preferably 2-3%.

It is desirable to adapt the number of perforations or holes per square metre such that the (flow per hole)×(holes per m$^2$) is constant at all points of the distributor or collector. It is desirable to achieve the same flow-per-m$^2$, and this means that the number of holes per m$^2$ may be adjusted such that (Flow-per-hole)×(holes per m$^2$)=constant at all points of the distributor.

For a distributor, flow-per-hole is proportional to the square root of (P1+P2−P3), where P1=inlet pressure at inside of the central distributor; P2=the pressure recovery in the distributor due to deceleration, from the Bernoulli equation (P+½ρv$^2$+ρgh=constant); and P3=the pressure outside of the distributor. P1 and P3 are fixed for a particular design, but P2 will vary along the length of the distributor from 0 to ½ρv$^2$. For the case where the holes are arranged in a regular triangular pattern then the number of holes per m$^2$ depend on the diameter of the hole and the desired free area. Thus for example, for 2.5% free area, the number of holes needed is 8018 holes per m$^2$ for holes of 2 mm diameter and 1282 holes per m$^2$ for holes of 5 mm diameter.

For a typical radial flow steam-raising methanol converter, the square root of (P1+P2−P3) may vary from about 123 to about 173 (a ratio of 1.41). This means that the required holes per m$^2$ may be varied between 8018 to 5670 for holes of 2 mm diameter (a ratio of 1/1.41) or 1282 to 906 for holes of 5 mm diameter (a ratio of 1/1.41). However, because varying the hole pitch on a hole-to-hole basis may not be practical, it is preferable to simply adjust the number on adjacent portions of the device by adjusting the holes per m$^2$ for each.

Where a layer of inert ceramic shaped units, such as ceramic balls, is placed between the distributor or collector and the catalyst or sorbent, the hole pitch can be similar to the depth of the layer of inert ceramic. For a 200 mm deep layer, the hole pitch may therefore be also 200 mm giving about 30 holes per m$^2$ for 5 mm holes.

The device may be sized according to the flowrate of process fluid. Thus the velocity at the open end or ends may be in the range 0.5 to 2 times the velocity in the connecting process pipework, but is most conveniently the approximately the same as the velocity in the connecting process pipework. For example, a fluid velocity of 20-40 metres per second.

The device comprises a plurality, e.g. 2-5 or more, columnar portions. The portions are joined together to form the device. The portions may be joined together outside the vessel in which they are to be installed or inside the vessel. Preferably the portions are joined together inside the vessel in which they are to be used. The length of the columnar portions may depend on the maximum allowable free-fall height of the catalyst or sorbent, or the weight of the portion. In addition to facilitating fabrication, using a plurality of portions facilitates a gentler loading of the catalyst or sorbent around the device in the vessel, thereby reducing the potential for breakage and dust formation. The lighter design of the present device allows for fewer, longer sub-assemblies than used for the prior art devices, which speeds up installation. In addition, different sub-assembly lengths may be provided, e.g. shortest to longest, in order to facilitate in-sequence assembly on site.

Joining options for the columnar portions include overlapping spigot joints and flange joints. An overlapping spigot joint may be formed using counter-sunk bolts and provides a relatively smooth joint. i.e. the joint does not extend significantly from the inside or outside surface of the device. Flange joints in contrast extend inside or outside of the device. Flange joints may be arranged either with the flange internal to the device or external to the device. The internal flange option, provides a relatively smooth external surface to the device but we have found creates a pressure drop within the device. The external flange option, although it provides a relatively smooth internal surface to the device, may be difficult to install through the man-holes typically present in reaction vessels and potentially creates voids in the beds of catalyst or sorbent under the flanges, which is undesirable.

We have found that a combination of overlapping spigot joints and internal flange joints offers improvements in the operation of the device compared to using internal flange joints alone. For example, if all of the joints were internal flanges, we have found that the pressure drop inside the device could be higher than the pressure drop across the perforations, meaning the pressure inside the device after a flange would be lower than the pressure in the bed of catalyst or sorbent adjacent to the previous section of the device leading to recirculation of process fluid, which is very undesirable.

Therefore in another arrangement, the means for controlling the flow of a gaseous process fluid to or from the device is the use of overlapping spigot joints to join portions of the device nearest an open end, and internal flange joints are used to join portions furthest from the open end.

For a bottom-entry vessel with a device having an open end at the bottom and a closed end at the top, this would mean that the overlapping spigot joints are used near the bottom of the device for joining the lower portions and internal flange joints for joining the upper portions. For a top-entry vessel with a device having an open end at the top and a closed end at the bottom, this would mean that the overlapping spigot joints are used near the top of the device for joining the upper portions and internal flange joints for joining the lower portions. For a double-entry vessel with a device having open ends at the top and bottom, this would mean that the overlapping spigot joints are used near the top and bottom of the device and flange joints near the middle of the device.

These arrangements are also superior to using just overlapping spigot joints throughout the device because the difference of pressure across the device is reduced leading to a better process fluid distribution within the bed of catalyst or sorbent. For example, in a top-entry vessel with a device having an open end at the top and a closed end at the bottom, if the final joint in the device near the open end is an overlapping spigot joint and the remaining joints are internal flange joints, there is a significant improvement in velocity variation and process fluid distribution through the bed of catalyst or sorbent.

In another arrangement, the means for controlling the flow of a gaseous process fluid to or from the device is the combination of providing a greater number and/or a larger size and/or a smaller spacing of the perforations in the inner screen in a portion adjacent the open end and the use of overlapping spigot joints to join portions of the device nearest an open end, and internal flange joints are used in a portion furthest from the open end.

The design of the present device also offers the potential for unique-shaped joints or bolt-patterns in the flanges so that the portions cannot be assembled in the wrong order. Moreover, the design reduces the risk of the device becoming misaligned or leaning within the reaction vessel.

The device is suitable for use as a distributor or collector in a radial-flow vessel. The invention therefore includes a radial-flow vessel containing the device.

The radial-flow vessel may be any design including a radial-flow vessel, including an axial-radial flow vessel. Such vessels may comprise a domed cylindrical shell with a process fluid inlet at one end and a process fluid outlet at the other end. A device as described above is connected to the inlet or outlet and extends along the longitudinal axis of the vessel from one end towards the other to provide a central void to which or from which a gaseous process fluid may flow. A peripheral void, which may be continuous or discontinuous, is also provided in the vessel to which or from which a gaseous process fluid may flow to the outlet or inlet. A fixed bed of catalyst or sorbent may be provided between the central and peripheral voids. A gaseous process fluid entering the vessel through the inlet may pass to the peripheral void, then radially inwards through the bed of catalyst or sorbent to the central void, in which case the device may be termed a collector, and then from the central void to the outlet. Alternatively, the gaseous process fluid entering the vessel through the inlet may pass to the central void, in which case the device may be termed a distributor, then radially outwards through the bed of catalyst or sorbent to the peripheral void, and then from the peripheral void to the outlet.

The device may be used as a collector or distributor, although in a preferred arrangement, the device is a distributor.

A bed of particulate catalyst or particulate sorbent may be provided between the central and peripheral voids. The radial thickness of the bed may be in the range 0.5-4.0 metres. The particulate catalyst or sorbent preferably has a maximum dimension, such as a width, diameter or length, in the range 2-25 mm, more preferably 2-15 mm, more preferably 2-7 mm. The catalyst or sorbent particles preferably have an aspect ratio, i.e. the longest dimension divided by the shortest dimension in the range 1-3.

The bed may be a particulate sorbent such as a hydrogen-halide sorbent, an organo-halide sorbent, a sulphur compound sorbent, a mercury sorbent or an arsenic sorbent. The process fluid may be any so-contaminated gas, such as natural gas, carbon dioxide, refinery off-gases, or mixtures thereof. Preferably the bed is a bed of a particulate catalyst. Particulate catalysts may suitably be selected from pre-reforming catalysts, water gas shift catalysts, methanol synthesis catalysts, ammonia synthesis catalysts, methanation catalysts and methanol oxidation catalysts. The process fluids for these catalysts may be any gas mixture suitable for reaction over these catalysts. The device and vessel are particularly suited to the reaction of synthesis gases containing hydrogen and carbon dioxide over methanol synthesis catalysts.

If desired, a layer of inert ceramic shaped units, such as ceramic balls, may be placed around at least part of the device to enhance diffusion of process fluid to or from the device. The depth of the layer may be in the range 50-500 mm, but is preferably 100-300 mm. The ceramic shaped units may have a maximum dimension such as width, length or diameter in the range 5-25 mm, preferably 10-15 mm. The ceramic shaped units preferably have an aspect ratio, i.e. the longest dimension divided by the shortest dimension in the range 1-2. Using larger perforations in the inner screen allows the full depth of the layer to be used to diffuse and mix process fluid jets associated with each perforation.

The catalyst or sorbent beds may be operated adiabatically or may be cooled or heated by a heat exchange medium passing through tubes or plates disposed within the bed of catalyst or sorbent. In the present invention, tube-cooled or plate-cooled beds are preferred.

In a preferred embodiment, the radial-flow vessel is a cooled radial-flow reaction vessel, in particular a radial-flow steam-raising converter (rSRC). In a rSRC, a gaseous process fluid, such as a synthesis gas, passes radially inwards or outwards through a bed of particulate catalyst which is cooled by a plurality of tubes or plates through which boiling water under pressure is fed as coolant. Such reactors are described, for example, in U.S. Pat. No. 4,321,234.

The invention further includes a process using the vessel containing the device. Thus a process using the vessel may comprise the steps of passing a process fluid to an inlet of a vessel, passing the process fluid from the inlet to the interior of the device, passing the process fluid from the device radially outwards through a bed of catalyst or sorbent to a peripheral void within the vessel, and passing the process fluid from the peripheral void to an outlet in the vessel. The bed of catalyst or sorbent is preferably cooled by a coolant passing through tubes or plates disposed within the bed of catalyst or sorbent. Alternatively, a process using the vessel may comprise the steps of passing a process fluid to an inlet of a vessel, passing the process fluid from the inlet to a peripheral void within the vessel, passing the process fluid from the peripheral void radially inwards through a bed of catalyst or sorbent to the interior of the device, and passing the process fluid from interior of the device to an outlet in the vessel. The bed of catalyst or sorbent is preferably cooled by a coolant passing through tubes or plates disposed within the bed of catalyst or sorbent.

Where the bed is a particulate sorbent, the process fluid may be any contaminated process stream containing a contaminant removed by the bed of sorbent, such as a hydrocarbon-containing gas. Alternatively, the process fluid may be a synthesis gas containing hydrogen.

Where the bed is a particulate catalyst, the process fluid may be any process stream containing reactants that react over the bed of catalyst. In a preferred embodiment, the process fluid is a synthesis gas comprising hydrogen. The synthesis gas comprising hydrogen may be a synthesis gas comprising hydrogen and carbon dioxide. Alternatively, the synthesis gas comprising hydrogen may be a synthesis gas comprising hydrogen and nitrogen.

In a preferred embodiment, the catalyst is a methanol synthesis catalyst, the process fluid is a synthesis gas comprising hydrogen, carbon monoxide and/or carbon dioxide, and the process is a methanol synthesis process.

The methanol synthesis catalysts are preferably copper-containing methanol synthesis catalysts, in particular the methanol synthesis catalyst is a particulate copper/zinc oxide/alumina catalyst. Particularly suitable catalysts are Mg-doped copper/zinc oxide/alumina catalysts as described in U.S. Pat. No. 4,788,175.

Methanol synthesis may be effected conventionally at elevated temperature and pressure, for example pressures in the range 20 to 120 bar abs and temperatures in the range 130° C. to 350° C.

The invention will be further described by reference to the figure in which.

It will be understood by those skilled in the art that the drawings are diagrammatic and that further items of equipment may be included in accordance with conventional chemical engineering practice.

Figure 1:
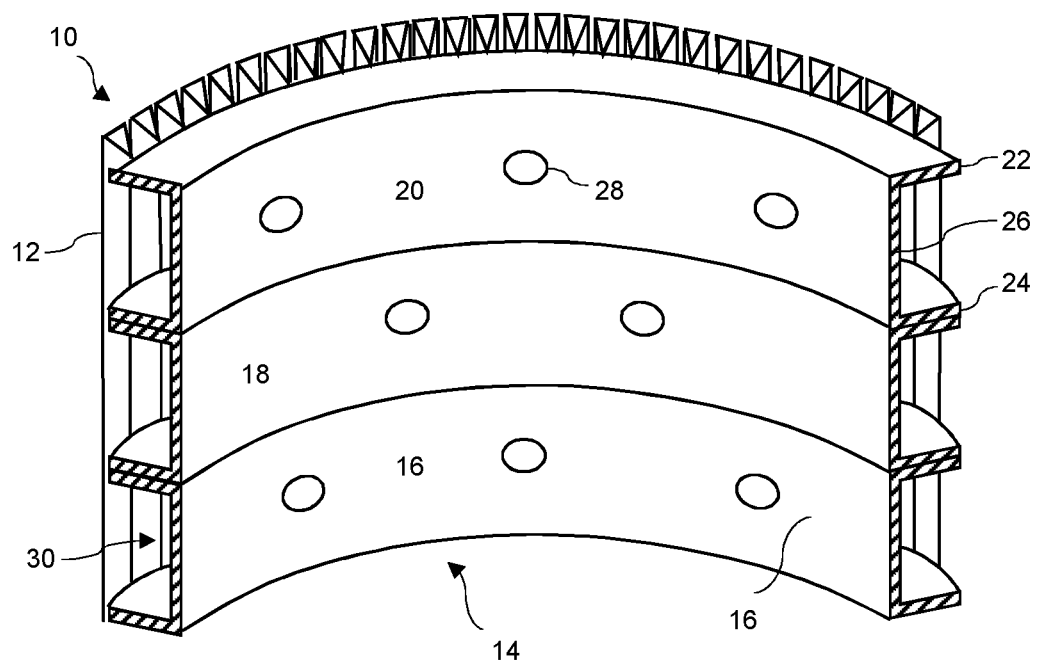
FIG. 1 is a cut-away depiction of part of a device according to the present invention.

In FIG. 1, a curved outer screen 10 is formed from a plurality of spaced parallel V-wires 12 arranged vertically on an inner screen 14 comprising three adjacent horizontal C-section support members 16, 18, 20. The apex of the V-wires 12 is in contact with upper 22 and lower 24 flanges of each C-section support. A web 26 connects the flanges of each support member. Each web comprises a plurality of spaced circular perforations 28. The perforations are arranged on the adjacent support members in a triangular pattern. Thus support members 16 and 20 each comprise three evenly-spaced perforations and the middle support member 18 has two perforations, each equidistant neighbouring perforations on the adjacent support member. The apex edge of the V-wires 12, along with the flanges 22, 24 and web 26 of each support member form a channel 30 in each support member.

A process fluid, such as a synthesis gas, is able to pass from the interior of the device through the perforations 28 in the support members 16, 18, 20 forming the inner screen 14, to the channels 30 between the webs 26 and the V-wires 12. The process fluid is also able to pass from the channels 30 through spaces between the V-wires 12 forming the outer screen 10, to the exterior of the device.

Similarly, the process fluid is able to pass in the opposite direction from the exterior of the device through the outer screen 10 and inner screen 14 to the interior of the device.

Figure 2:
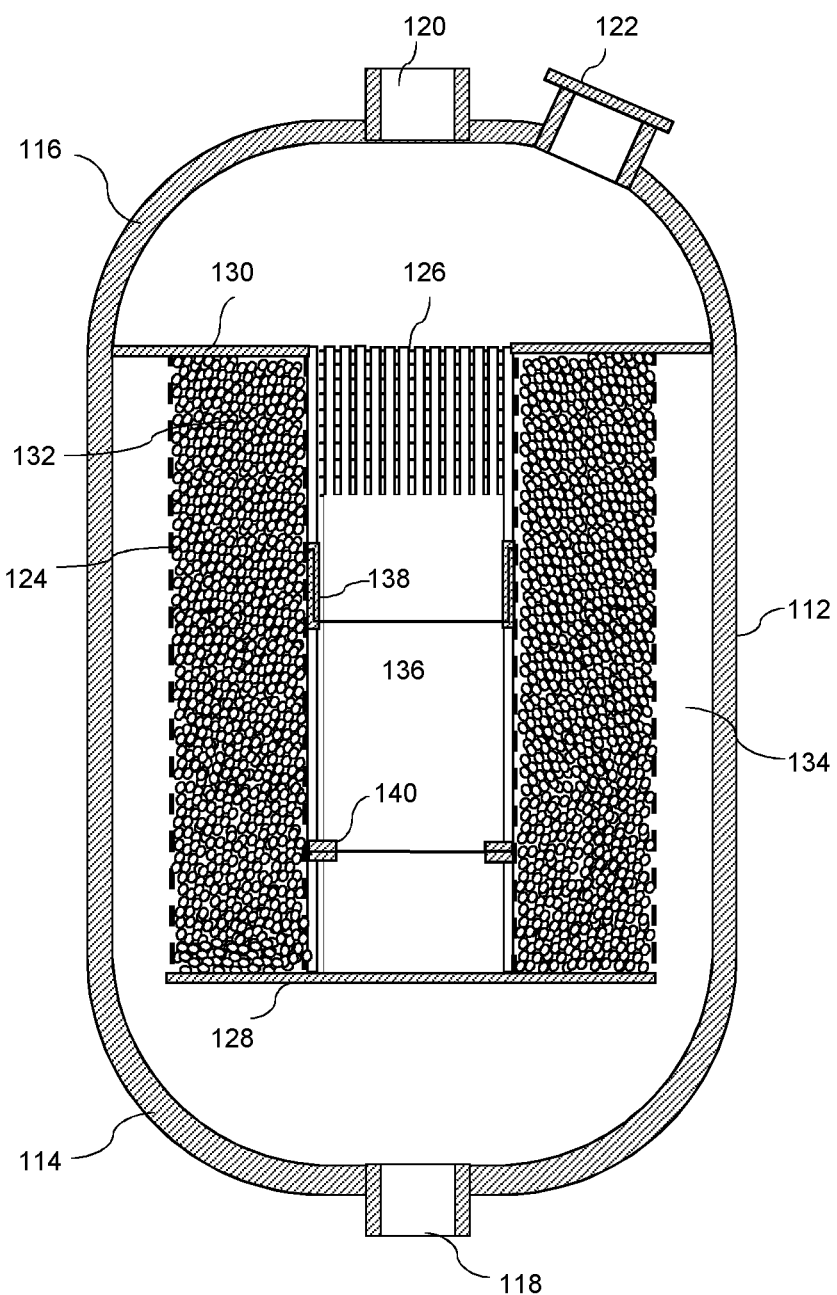
FIG. 2 is a cross-section of a radial-flow vessel containing a device and illustrating a preferred joint arrangement.

In FIG. 2, a vessel adapted for outward radial flow comprises an elongate cylindrical shell 112 aligned vertically with a first domed end 114 at the bottom and a second domed end 116 at the top. The first end 114 has a process fluid outlet pipe 118 positioned in line with the vertical axis of the vessel. The second end 116 has a process fluid inlet 120 also positioned in line with the vertical axis of the vessel and an adjacent catalyst loading port 122.

The shell 112 contains a perforate cylindrical collector 124 and a device 126 as described herein as a distributor. The collector 124 and distributor 126 are arranged coaxially within the shell and are mounted between a first non-perforate circular baffle plate 128 near the first end 114 and a second non-perforate annular baffle plate 130 near the second end 116. The distributor has an open end formed by the annular baffle 130 and a closed end formed by the circular baffle 128. A particulate catalyst, e.g. a particulate methanol synthesis catalyst 132, is disposed between the collector 124, distributor 126 and baffle plates 128, 130. The diameter of the circular baffle plate 128 is about that of the collector 124. The annular baffle plate 130 extends from the inside of the shell 112 to the outer edge of the distributor 126. A peripheral void 134 is formed between the outside of the collector 124 and the inside wall of the shell 112. A central void 136 is formed within the distributor 126.

The distributor 126 is depicted with an upper section having an outer screen formed by a plurality of parallel, vertical, spaced V-wires. The lower section is cut-away to depict the interior of the device. The distributor comprises three portions. The uppermost portion is joined to the middle portion by an overlapping spigot joint 138. The lower portion is connected to the middle portion by an internal flange joint 140.

In use a process fluid, such as a synthesis gas containing hydrogen and carbon oxides is fed into the vessel via the process fluid inlet 120 and is directed by baffle plate 130 to the distributor 126 and then to the central void 136. Baffle plate 130 prevents by-pass of the process fluid around the catalyst bed 132. The process fluid passes radially outwards from the distributor 126 through the catalyst bed 132 to the collector 124 and peripheral void 134. The resulting reacted process fluid is then directed from the peripheral void 134 to the process fluid outlet 118, from which the reacted process fluid may be recovered.

The invention is further described by reference to the following Examples.

EXAMPLE 1

The pressure profile in a 10-metre length distributor as depicted in FIGS. 1 and 2 having 5 portions and 4 joins was determined for a methanol synthesis gas using the Bernoulli equation; pressure energy+velocity energy+elevation energy=constant; i.e.

$$P + \tfrac{1}{2}\rho v^2 + \rho g h = \text{constant}$$

At the entry to the distributor, the velocity is at its maximum and the velocity energy term is high. The elevation energy change is small so almost all of the reduction in velocity energy is offset by an increase in the pressure energy.

For a distributor having only a smooth internal surface (i.e. no flange joints) this results in a pressure difference ($P_{MAX} - P_{MIN}$) along the distributor of 14 kPa. If all of the joints used internal flanges a large initial pressure drop of about 20 kPa occurs with lower pressure drops at each subsequent flange joint. If the perforations provide a 15 kPa pressure drop, then the pressure inside the bottom section of the distributor is lower than the pressure in the catalyst bed associated with the adjacent section. This leads to a recirculation flow, with some gas flowing from the catalyst bed back into the bottom section of the distributor.

When a mix of overlapping spigot joints for the top portion, and internal flanges for the lower portions is used, the overall ($P_{MAX} - P_{MIN}$) is reduced, which leads to a better gas distribution through the catalyst bed than when overlapping spigot joints are used for every section, and significantly better than when using internal flanges for every joint.

Figure 3:
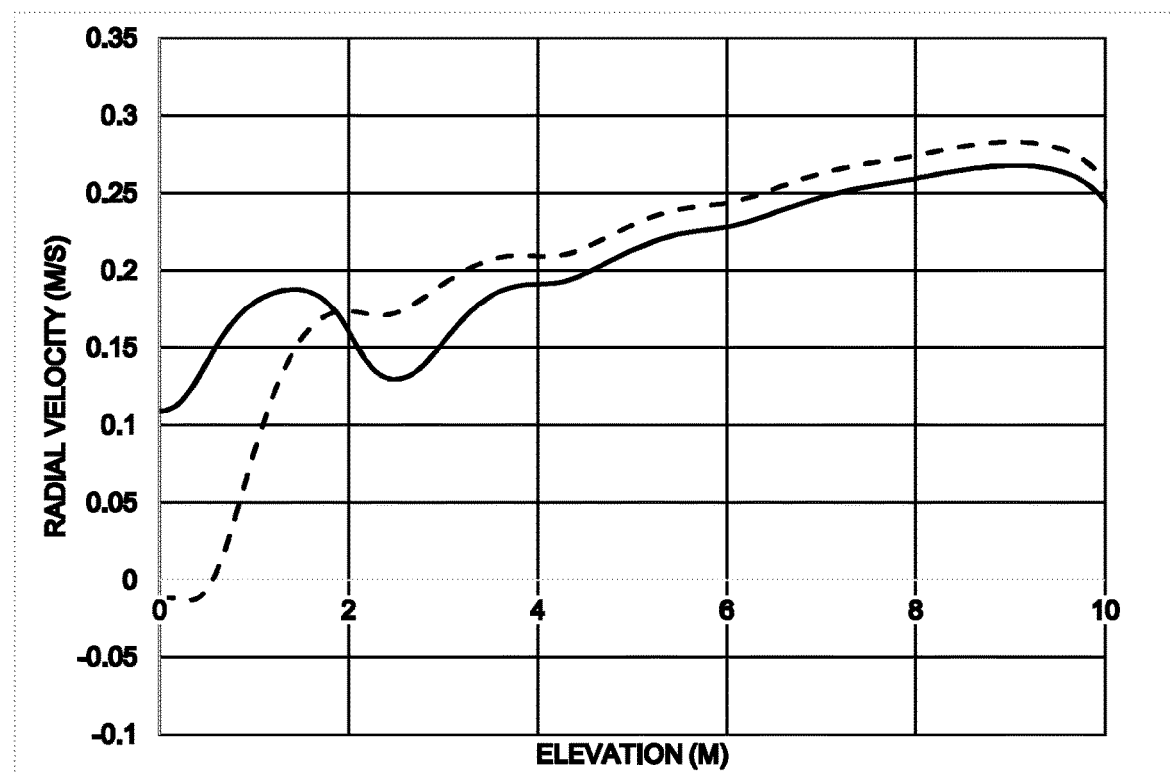
FIG. 3 is a graph depicting radial velocity along the elevation of different devices in a radial-flow vessel.

In FIG. 3 the velocity profile for two cases is compared. The velocity profile for internal flanges for all distributor sections is depicted by the dotted line. The velocity profile for overlapping spigot joint between sections 1 and 2, and the remaining joints all internal flanges is depicted by the solid line. The undesirable recirculation effect is seen as a negative velocity for the dotted line. By replacing the first joint with an overlapping spigot joint there is a significant improvement in the velocity variation. Further through the catalyst bed the flow variation becomes even smaller.

The invention claimed is:

1. A device suitable for use as a distributor or collector in a radial-flow reaction vessel, the device comprising an open end and a plurality of rigid columnar portions,
   each columnar portion comprising a cylindrical outer screen formed from parallel spaced wires and a perforate inner screen fixed to the outer screen, said inner screen formed from a plurality of adjacent perforate support members that support the spaced wires,
   wherein the rigid columnar portions further comprise a means for controlling a flow of a gaseous process fluid to or from the device,
   wherein the means for controlling the flow of a gaseous process fluid to or from the device comprises the use of overlapping spigot joints to join portions of the device nearest the open end, and internal flange joints to join portions furthest from the open end.

2. The device of claim 1, wherein the means for controlling the flow of the gaseous process fluid to or from the device further comprises is providing a greater number and/or a larger size and/or a smaller spacing of the perforations in the inner screen in a portion adjacent the open end.

3. The device of claim 1, wherein the wires have cross-sections that are circular, square, rectangular, triangular or polygonal.

4. The device of claim 3, wherein the triangular or wedge-shaped bars or wires are arranged with the apex of the triangle or wedge faces directed inwardly towards the centre of the device.

5. The device of claim 1, wherein the support members are spaced apart with a maximum spacing between the support members in the range of from 1 mm to 10 mm.

6. The device of claim 1, wherein the support members are adjacent with no separation.

7. The device of claim 1, wherein each support member comprises two spaced attachment points and a curved or polygonal portion connecting the attachment points and extending towards the interior of the device.

8. The device of claim 1, wherein the support members have a cross-section that is a semi-circle, an L-section comprising first and second flanges, or a C-section comprising first and second flanges separated by a web, each flange optionally having a lip.

9. The device of claim 1, wherein the device is prepared from rigid columnar portions having a diameter in the range of from 0.45 metres to 0.65 metres.

10. The device of claim 1, wherein the device is prepared from rigid columnar portions having a length in the range of from 1 metres to 3 metres.

11. A radial-flow vessel containing the device of claim 1.

12. The radial-flow vessel of claim 11 comprising a domed cylindrical shell with a process fluid inlet at one end and a process fluid outlet at the other end, the device connected to the inlet or outlet and extending along the longitudinal axis of the vessel from one end towards the other to provide a central void to which or from which the process fluid may flow, a peripheral void to which or from which a process fluid may flow to the outlet or inlet and a fixed bed of catalyst or sorbent between the central and peripheral voids.

13. The radial-flow vessel of claim 11 containing a methanol synthesis catalyst.

14. The radial-flow vessel of claim 11 that is a cooled radial-flow reaction vessel.

15. A process using the radial-flow vessel of claim 11, the process comprising:
   (a) passing a process fluid through an inlet of the vessel;
   (b) passing the process fluid from the inlet into the device;
   (c) passing the process fluid from the device radially outwards through a bed of catalyst or sorbent to a peripheral void within the vessel, and (d) passing the process fluid from the peripheral void to an outlet of the vessel.

16. The device of claim 1, wherein the support members are spaced apart with a maximum spacing between the support members in the range of from 2 mm to 4 mm.

17. The device of claim 1, wherein the device is prepared from rigid columnar portions having length in the range of from 1.5 metres to 2.0 metres.

18. The radial-flow vessel of claim 11, wherein the radial-flow vessel is a radial-flow steam-raising converter (rSRC).

* * * * *